United States Patent [19]

Bird

[11] 4,197,843

[45] Apr. 15, 1980

[54] VOLUME LIMITING VENTILATOR

[75] Inventor: Forrest M. Bird, Palm Springs, Calif.

[73] Assignee: Minnesota Mining and Manufacturing Company, St. Paul, Minn.

[21] Appl. No.: 892,677

[22] Filed: Apr. 3, 1978

[51] Int. Cl.² .......................................... A61M 16/00
[52] U.S. Cl. ........................ 128/200.14; 128/203.14; 128/204.25; 128/204.26; 128/205.14; 128/205.15; 128/205.16
[58] Field of Search .................... 128/145.5–145.8, 128/188, 194

[56] References Cited

U.S. PATENT DOCUMENTS

| | | | |
|---|---|---|---|
| 3,156,238 | 11/1964 | Bird et al. | 128/145.6 |
| 3,307,542 | 3/1967 | Andreasen | 128/145.8 |
| 3,537,448 | 11/1970 | Liston | 128/145.5 |
| 3,537,449 | 11/1970 | Foxwell et al. | 128/145.5 |
| 3,817,246 | 6/1974 | Weigl | 128/145.8 |
| 3,851,645 | 12/1974 | Connel | 128/145.6 X |
| 3,916,889 | 11/1975 | Russell | 128/145.8 |
| 4,020,834 | 5/1977 | Bird | 128/145.6 |

Primary Examiner—Henry J. Recla

[57] ABSTRACT

A volume limiting ventilator having a sequencing servo for switching from an inhalation phase to an exhalation phase in its operative cycle. A bellows mounted in a container is provided for receiving gas from a source of gas under pressure. A master venturi is in communication with the interior of the bellows and the exterior of the bellows. A large air breathing tube forming a part of a breathing circuit connects the interior of the bellows to a patient adapter. A master flow cartridge controlled by the sequencing servo supplies source gas to the master venturi. A transfer valve assembly is provided for determining whether the gas flows straight through to the breathing circuit or alternatively is supplied to the container carrying the bellows to raise the bellows. The transfer valve assembly controls the transfer of gas in the container from the exterior of the bellows to the interior of the bellows. A volume stabilizer is provided for stabilizing the volumes between the interior of the bellows and the exterior of the bellows at the termination of the inspiratory phase. An expiratory nebulization cartridge is provided for supplying expiratory nebulization.

21 Claims, 3 Drawing Figures

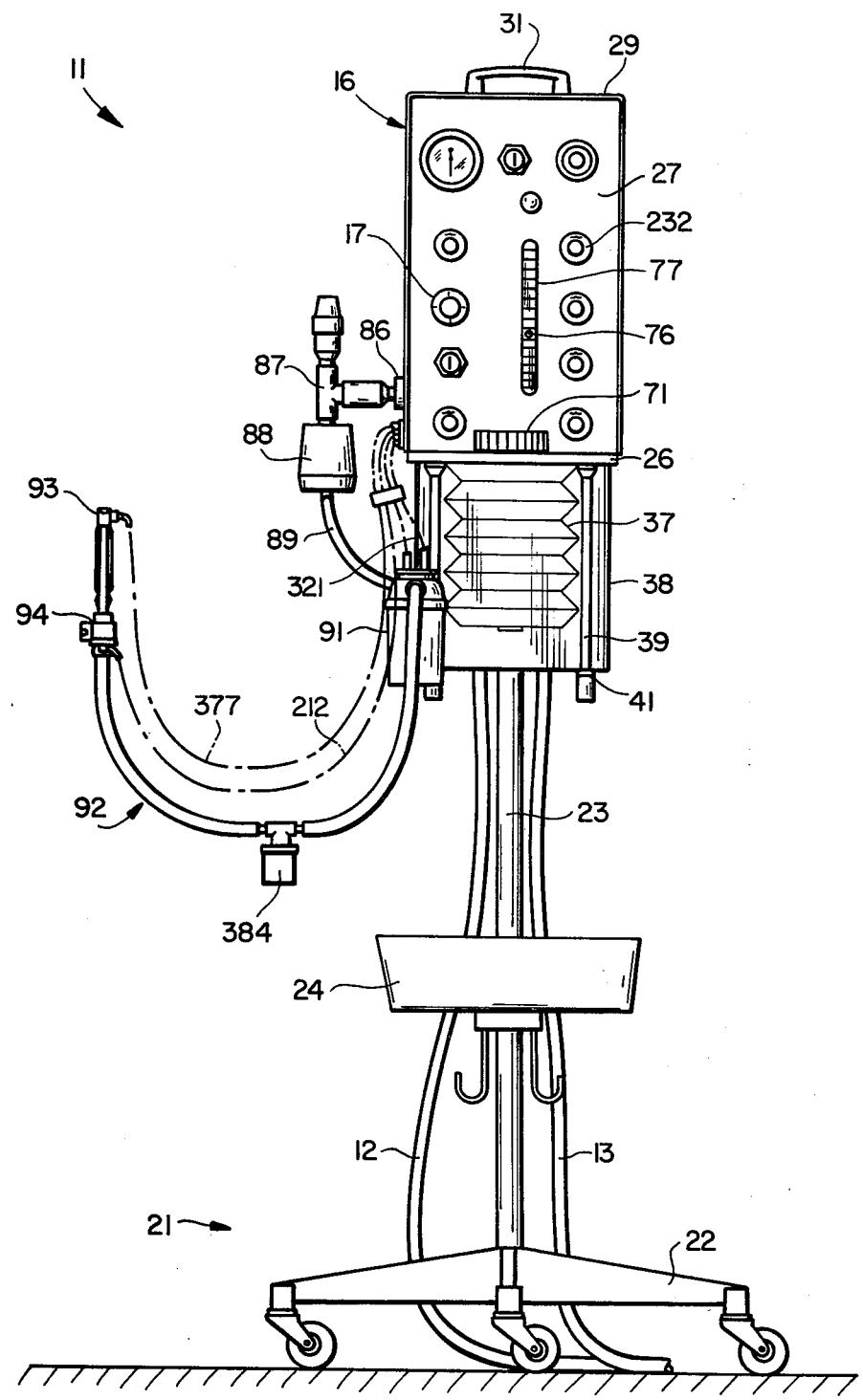
FIG_1

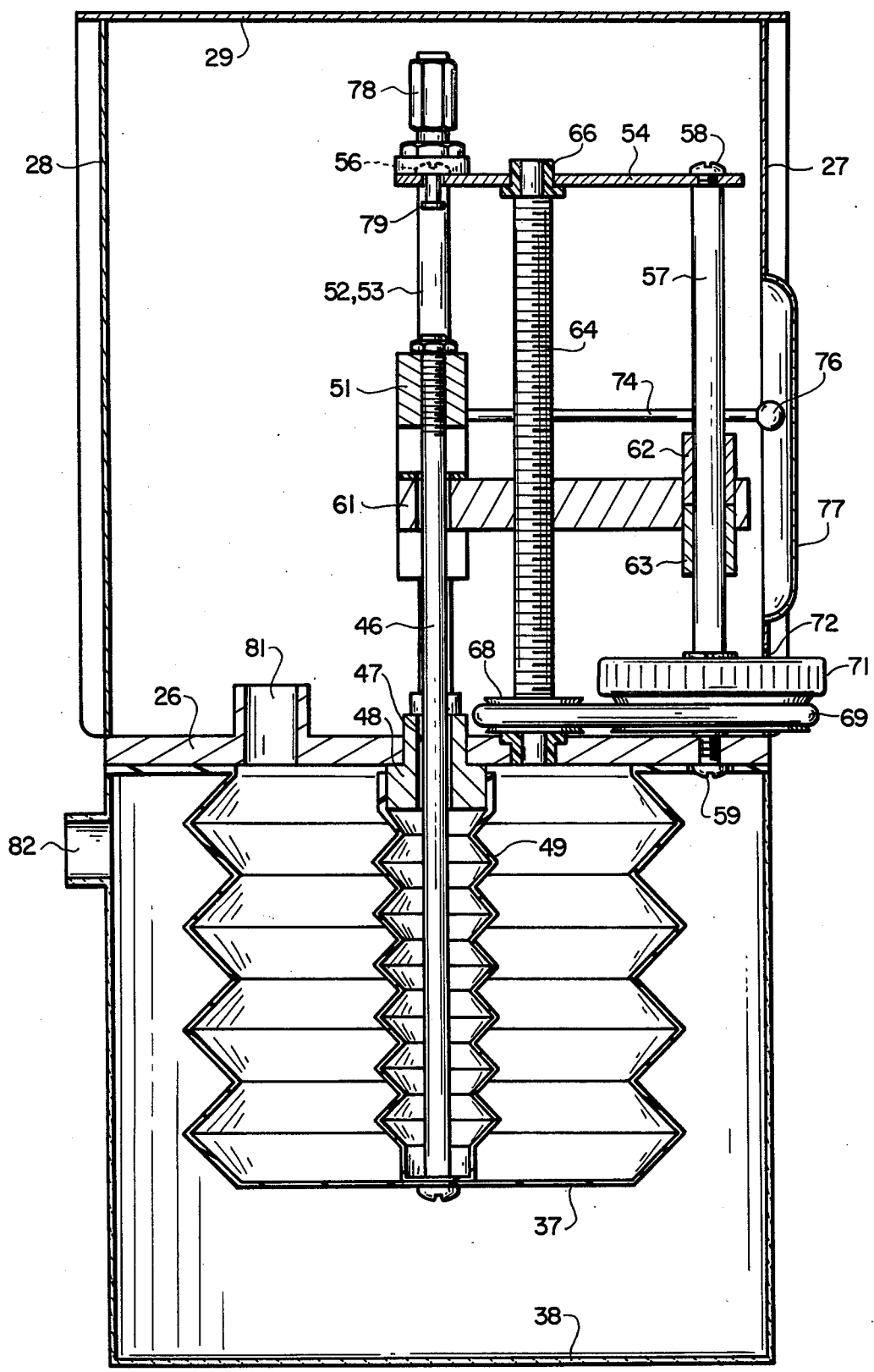
FIG_2

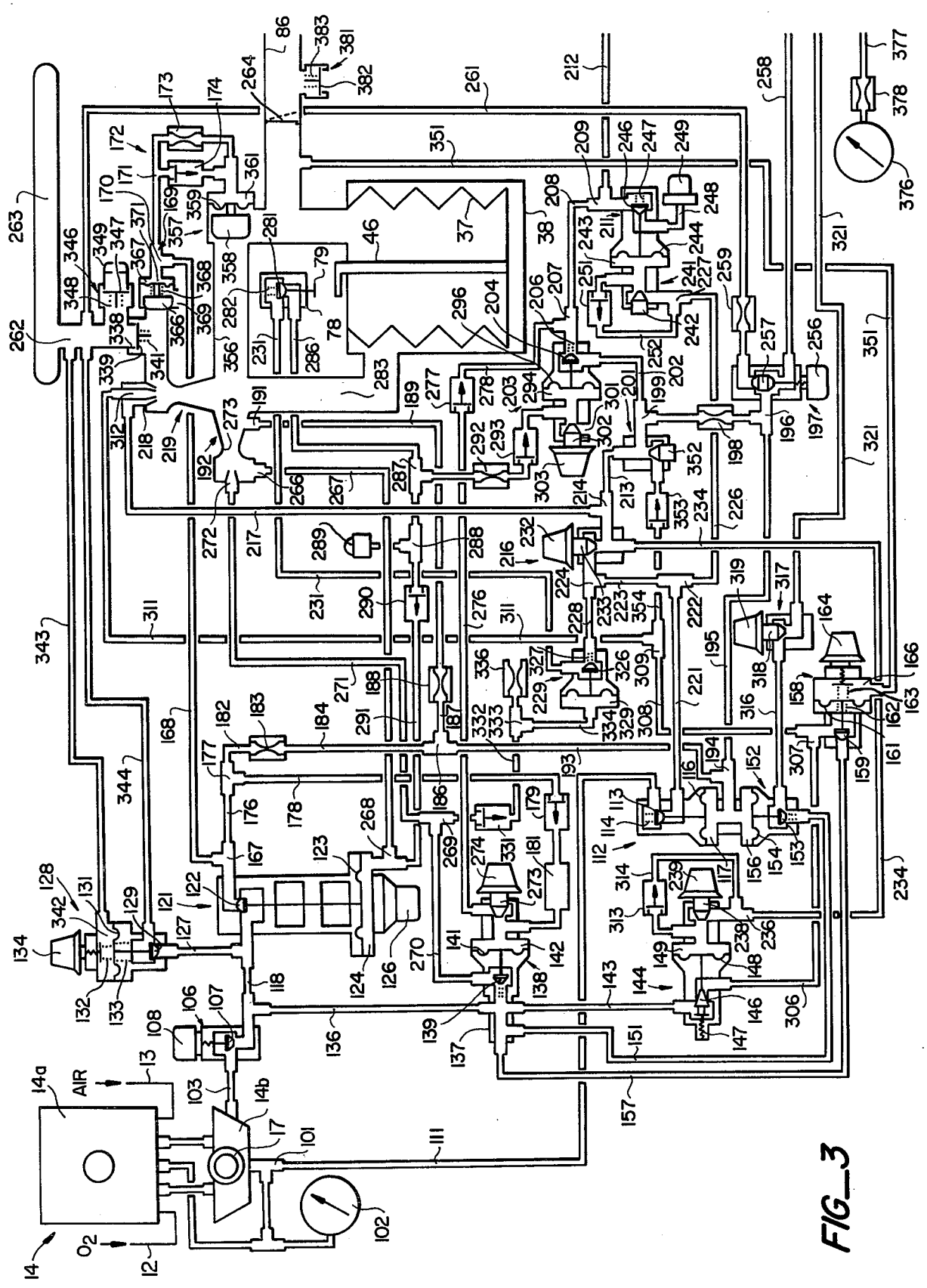
FIG_3

VOLUME LIMITING VENTILATOR

BACKGROUND OF THE INVENTION

Volume limiting ventilators have heretofore been provided as, for example, disclosed in U.S. Pat. Nos. 3,530,856 and 4,020,834. However, there is a need to provide an updated volume limiting ventilator providing additional features such as selectable nebulization, failsafe devices and other features normally associated with non-volume limiting ventilators. There is, therefore, a need for a new and improved volume limiting ventilator.

DESCRIPTION OF THE PREFERRED EMBODIMENT

As shown in FIG. 1, the ventilator 11 of the present invention is adapted to be connected to a source of gas under a suitable pressure as, for example, oxygen and air under 50 psi. For example, as shown in FIG. 1, the ventilator is supplied with oxygen through a tube 12 at a pressure of 50 psi and air through a tube 13 at a pressure of 50 psi. The tubes 12 and 13 are connected to a blender 14 (FIG. 3) of a suitable type such as that described in U.S. Pat. No. 3,737,627. The blender 14 has been separated into two parts, 14a and 14b, and is mounted within the case 16. The part 14a can be identified as a main module whereas the part 14b can be identified as a mixer module. The valve module 14b has a control knob 17 accessible from the exterior of the case for adjusting the oxygen concentration in the gas supplied by the blender 14.

The case 16 (FIG. 1) is mounted upon a support stand 21 which is provided with a four-legged castered base 22 and an upright support member 23. A tray 24 is mounted on the upright support member 23 below the case 16.

The case 16 consists of a base plate 26 usually provided with an ear that carries a hub (not shown) mounted upon the upright support member 23. The case is provided with a front and rear walls 27 and 28 and a "U" shaped member 29 which fits over the sides of the front and rear walls 27 and 28 to provide a box-like enclosure overlying the base plate 26. A handle 31 is mounted upon the U-shaped member 29.

A bellows assembly is mounted below the base plate 26 and includes a cylindrically shaped convoluted bellows 37 which is enclosed within a cylindrical canister 38. The canister 38 is held in place by four depending rods 39 secured to the base plate 26 and which carry removable braces 41 that are adapted to engage the bottom side of the canister 38 in the manner described in U.S. Pat. No. 3,530,856. The canister 38 is preferably formed of a suitable transparent material such as plastic so that movement of the bellows 37 within the canister can be visually observed. By clamping the canister 38 in place by the use of the braces 41, the upper margin of the bellows 37 is also clamped to the base plate 26 so that a seal is formed between the upper extremity of the bellows 37 and the interior of the canister 38.

Means is provided for adjusting the amount of gas which can be entrained within the bellows 37 and consists of a push rod 46 (FIG. 2) which has its lower extremity secured to the lower extremity of the bellows 37. As shown in FIG. 2, the push rod 46 extends upwardly through a hole 47 provided in a bushing 48 carried by the deck or base plate 26. A seal is formed between the push rod 46 and the interior of the bellows and consists of a small convoluted bellows 49 surrounding the push rod and having its lower end engaging the lower extremity of the bellows and having its upper end engaging the hub or bushing 48. A counter-weight 51 is secured to the upper end of the push rod 46. The counter-weight 51 travels on spaced apart parallel guide rods 52 and 53 which have their lower extremities threaded into the deck or base plate 26. A support plate 54 is secured to the upper ends of the guide rods 52 and 53 by screws 56. The support plate 54 is triangularly shaped and has its apex portion secured to another guide rod 57 by a screw 58. The lower extremity of the guide rod 57 is secured to the deck plate by a screw 59. A volume limiting arm 61 is slidingly mounted upon the guide rod 57 and carries upper and lower bushings 62 and 63 which serve as stops as hereinafter described. The volume limiting arm 61 is threaded onto a jack screw 64. The upper end of the jack screw 64 is rotatably mounted in a bushing 66 formed of suitable material such as Delrin provided in the support plate 54. Similarly, the lower end of the jack screw 64 is rotatably mounted in another bushing (not shown) also formed of a suitable material such as Delrin.

Means is provided for rotating the jack screw 64 for causing raising and lowering of the volume limiting arm 61 and consists of a small pulley 68 formed of a suitable material such as Delrin which is secured to the jack screw and which is driven by an "O" ring 69. The "O" ring 69 is driven by a large volume limiting dial or thumb wheel 71 which is rotatably mounted upon the guide rod 57 and is held in a predetermined position on the guide rod 57 by suitable means such as a "Tru-arc" retaining ring (not shown). The thumb wheel 71 is of such a size that a portion thereof extends through a slot 72 provided in the front wall 27. A rod 74 is mounted upon the counterweight 51 and extends forwardly therefrom and carries a small ball 76. The ball is adapted to travel in a window 77 which is generally U-shaped in cross section and which is mounted in the front wall 27. The ball 76 serves as an indicator to indicate the volume of gas within the bellows in accordance with calibrations provided on the window 77. A volume termination switch 78 is mounted upon the support plate 54 and is provided with an operating arm 79 which is adapted to be engaged by the portion of the push rod 46 extending through the counterweight 51.

It can be seen that by adjusting the volume limiting dial 71, the volume limiting arm 61 can be moved upwardly and downwardly by rotation of the jack screw 64 to adjust the position of the volume limiting arm 61. The upper and lower limits of the adjustment of the arm 61 are determined by when the bushing 62 engages the support plate 54 and when the bushing 53 engages the volume limiting dial 71. After the volume limiting arm 61 has been placed in a predetermined position by adjustment of the volume limiting dial 71, the lowermost amount of travel of the push rod 46 is determined by when the counterweight 51 carried by the push rod 46 engages the volume limiting arm and prevents further downward travel of the push rod. Thus it can be seen that it is possible to readily adjust the volume of gas which is to be received by the bellows and to be utilized during the next inspiratory phase.

As shown in FIG. 2, the bellows is provided with an inlet 81 and the canister is provided with an inlet 82. The ventilator is provided with an outlet 86 (FIG. 1) which is connected to piping 87. The piping 87 is connected to a filter 88 and the filter 88 is connected by piping 89 to a nebulizer 91 of a conventional type. The nebulizer 91 is connected to a breathing tube assembly 91 of a conventional type which includes a patient adapter in the form of an endotracheal fitting 93 and exhalation valve assembly 94 also of a conventional type.

Operation and use of the ventilator may now be briefly described in conjunction with the schematic diagram which is shown in FIG. 3. Let is be assumed that a source of gas under suitable pressure such as 50 psi in the form of oxygen and air is supplied to the tubes 12 and 13, respectively, and to the blender 14. The control knob 17 forms a part of the mixer module and is provided for adjusting the mixture of oxygen and air which is supplied to an outlet tee 101. One leg of the outlet tee 101 is connected to a manometer or pressure gauge 102 for measuring the source gas pressure. Thus, it can be seen that the manometer 102 provides a measure of the pressure at the outlet from the blender 14. Source gas is also supplied from the mixer module 14b through a tube 103 to a master rotary on-off switch 106 which is provided with a valve member 107 movable between open and closed positions to control the flow of gas from the inlet to the outlet of the switch by operation of a control knob 108.

The tee or fitting 101 is connected by a tube 111 to the inlet of a normally closed master flow cartridge 112. The cartridge 112 is provided with a valve member 113 movable between open and closed positions to control the flow of gas from the inlet to the outlet. It is yieldably urged into a closed position by a spring 114. The valve member 113 is adapted to be moved to an open position against the force of the spring 114 by a diaphragm 116. The master on-off cartridge 112 is formed with a chamber 117 which is adapted to be filled with gas to apply a force to the diaphragm 116 to move the valve member 113 to the open position.

When the rotary on-off switch 106 is turned to the "on" position, gas is supplied from the blender 14 through a tube 118 to the inlet of a sequencing servo 121. The sequencing servo is of the type described in U.S. Pat. No. 3,915,164. As disclosed therein, it includes a valve member 112 movable between open and closed positions to control the flow of gas from the inlet to the outlet. A diaphragm 123 is connected to the valve member 122 and is provided for moving the same between open and closed positions. A chamber 124 is formed in the sequencing servo 121 on one side of the diaphragm 123 which is used for operating the diaphragm 123 as hereinafter described. A compound knob assembly 126 forms a part of the sequencing servo 121 and is provided for adjusting the same.

Source gas is also supplied from the tube 118 through a tube 127 to the inlet of an entrainment reservoir refill servo cartridge 128. It also is provided with a valve member 129 movable between open and closed positions for controlling the flow of gas from the inlet to the outlet. The operation of the valve member 121 is controlled by a diaphragm 131 and a pair of springs 132 and 133 and a control knob 134 for adjusting the force supplied by the springs 132 and 133 to the diaphragm.

Source gas is also supplied from the master on-off switch 106 through a tube 136 to a manifold 137. The manifold 137 is connected to the inlet of an expiratory time control cartridge 138. This cartridge also includes a valve member 139 movable between open and closed positions for controlling the flow of gas from the inlet to the outlet and is controlled by diaphragm 141. A chamber 142 is formed on one side of the diaphragm which is adapted to be supplied with gas as hereinafter described. The manifold 137 is connected by tube 143 to the inlet of a flow accelerator cartridge 144. This cartridge 144 is provided with a valve member 146 which is normally urged into a closed position by a spring 147 for controlling the flow of gas from the inlet to the outlet. A diaphragm 148 is provided for moving the valve member 146 to an open position against the force of the spring 147. A chamber 149 is formed on one side of the diaphragm and is adapted to be supplied with gas as hereinafter described. The manifold 137 is connected by a tube 151 to the inlet of an expiratory flow cartridge 152 which also includes a valve member 153 movable between open and closed positions to control the flow of gas from the inlet to the outlet and a diaphragm 154 for controlling the operation of the valve member. A chamber 156 is formed on one side of the diaphragm and is adapted to be filled with gas as hereinafter described. The manifold is also connected by tube 157 to the inlet of a baseline constant positive airway pressure cartridge (CPAP cartridge) 158. This cartridge also includes a valve member 159 movable between open and closed positions to control the flow of gas from the inlet to the outlet. Movement of the valve member is controlled by diaphragm 161 which is engaged by springs 162 and 163, the force of which can be adjusted by a control knob 164. A chamber 166 is formed on one side of the diaphragm 161 and is adapted to be filled with gas as hereinafter described.

Let it be assumed that the sequencing servo 121 is turned on as hereinafter described to commence the inspiratory phase by having the valve member 122 move to the open position to permit gas to flow from the blender 14 through the master on-off switch 106 through the inlet of the sequencing servo 121 and to the outlet manifold 167 which delivers source gas through a tube 168 and tee 170 to a volume stabilizer cartridge 169 and also by tube 171 to a post-inspiratory wedge circuit 172 which consists of a flow restricting orifice 173 and a one-way check valve 174. The outlet of manifold 167 of the sequencing servo 121 is also connected by a tube 176 to a tee 177. One leg of the tee 177 is connected by tube 178 through a one-way check valve 179 through a reservoir 181 to the chamber 142 of the expiratory time control cartridge 138. Source gas is also supplied through the other leg of the tee 177 through a tube 182 through an expiratory timer preferential loading orifice 183 through a tube 184 to a tee 186. One leg of the tee is connected by tube 187 to a fail-safe bleed-down orifice 188 and then through a tube 189 into the accessory sensing port 191 of the sensing/servoing venturi assembly 192. The other leg of the tee 186 is connected by a tube 193 to a twin manifold 194 provided for the chambers 117 and 156 of the master flow cartridge 112 and the expiratory flow cartridge 152. Gas is supplied from this twin manifold through a tube 195 to the inlet manifold 96 of the inspiratory nebulizer humidifier selector switch 197. Gas is also supplied from the manifold 196 through the minimal inspiratory flow orifice 198 to the inlet manifold 199 of the demand CPAP sensitivity orifice 201. Gas is also supplied from the manifold 199 through a tube 202 to the inlet of the normally open post-inspiratory hold timing cartridge 203. The cartridge 203 is provided with a valve member 204 normally held in an open position by a spring 206. The valve member 204 is movable between open and closed positions to control the flow of gas from the inlet to the outlet. The cartridge 203 is provided with an outlet manifold 207. The manifold 207 is connected by a tube 208 to an inlet manifold 209 of the inspiratory flow and fail-safe lock-out cartridge 211. Gas is also supplied from the manifold 209 through a tube 212 which is connected to the exhalation valve assembly 94 to maintain it in a closed position during the inspiratory phase.

Source gas is also supplied from the demand CPAP sensitivity orifice 201 through a tube 213 to an inlet manifold 214 of a flow control valve assembly 216. Gas is supplied from the manifold 214 through a tube 217 to the dual outer jets 218 of the master venturi assembly 219 to provide minimal inspiratory flow of gases to the patient.

As soon as source gas is delivered to the dual manifold 194 of the master flow cartridge 112 and the expiratory nebulization cartridge 152, the master flow cartridge 112 is servoed "on". As pointed out previously, the inlet of the master flow cartridge 112 is connected directly to the blender 101 through the tube 111 and delivers gas through its outlet through a tube 221 to a tee 222. One leg of the tee 222 is connected by a tube 223 to an inlet manifold 224 of the flow rate control valve assembly 216. Another leg of the tee 222 is connected by a tube 226 to inlet manifold 227 of the inspiratory flow and fail-safe lock-out 211. Source gas is supplied from the manifold 224 through a tube 228 to the inlet of a volume sequencing delay cartridge 229 which is normally open to supply gas at its outlet through a tube 231 to the volume termination switch 78.

From the foregoing, it can be seen that minimal inspiratory flow is provided by the sequencing servo 121 through the minimum inspiratory flow orifice 198 which delivers gas through the dual jets 218 of the master venturi assembly 219. The principal flow of inspiratory gas, however, is through the master flow cartridge 112 to the manifold 224 of the flow rate control valve assembly 216 which includes a control knob 232 for adjusting the position of a needle valve 233 to control the rate of flow through the manifold 214 to the tube 217 into the dual jets 218 of the master venturi assembly 219. As the needle valve 233 is opened, the inspiratory flow rate and the inspiratory servoing pressures are proportionally increased. Source gas is also supplied from the flow rate control valve assembly 216 through a tube 234 to a manifold 236 of the flow accelerator cartridge 237. The gas is delivered at a metered rate into the chamber 149 under the control of a needle valve 238, the position of which can be adjusted by rotation of the knob 239. Metered inspiratory flow of source gases is supplied through the manifold 199 and then through the normally open post-inspiratory hold timing cartridge 203 to maintain inspiratory competency of the exhalation valve 94 and the post-inspiratory hold/expiratory timer interlock device 203. The minimal inspiratory flow orifice 198 serves to provide communication between the inspiratory flow from the sequencing servo 121 and the master flow cartridge 112 which delivers gas to the inspiratory flow rate valve assembly 216. Since they share a common source of gas from the blender 14, gas pressures in each circuit under normal inspiratory conditions should be approximately equal. Should the inspiratory flow rate valve assembly 216 be in the closed position, minimal flow and inspiratory servoing would be accomplished by inspiratory flow of gases from the sequencing servo 121. All inspiratory functions would still be performed except flow acceleration. Flow acceleration would not occur because the inspiratory flow of gases is metered through the expiratory timer preferential loading orifice 183 and through the fail-safe bleed-down orifice 188 to the accessory port 191 of the sensing/servoing venturi. Under such conditions, there will be insufficient pressure created by back flow to activate the flow accelerator cartridge 144. With the inspiratory flow rate valve assembly 216 closed, the servoing pressure of source gas being supplied through the master flow cartridge 112 is supplied to the timing circuit 241 of the inspiratory flow fail-safe lock-out cartridge 211.

This timing circuit 241 includes a needle valve 242 to control the flow of gas from the manifold 227 into a chamber 243 formed on one side of a diaphragm 244. The diaphragm 244 is connected to a valve member 246 movable between open and closed positions against the force of a spring 247 to control the flow of gas from the inlet manifold 209 to the outlet 248. The outlet 248, if desired, can be connected to a whistle type alarm 249 open to the atmosphere as shown. The timing circuit 241 also includes a one-way check valve 251 which is connected by a tube 252 to the manifold 227. This condition of supplying additional gas under pressure to the chamber 243 could cause the valve member 246 to be moved to an open position to bleed gas from the line 212 to permit the exhalation valve assembly to open and to cause a premature lock-out.

At the termination of mechanical inspiration as hereinafter described, the flow circuit through the expiratory timer preferential loading orifice 183 and the circuit to the timing circuit 241 can be bled down through the dual jets 218 of the master venturi assembly 219, through the fail-safe bleed-down orifice 188 and through the inspiratory nebulizer/humidifier circuit hereinafter identified.

Means is provided for selecting inspiratory nebulization and humidification and consists of a rotary three-way switch which previously has been identified as the inspiratory nebulizer/humidifier selector 197. As pointed out previously, source gas is supplied from the sequencing servo 121 to the manifold 196. Gas supplied to the manifold 196 can be directed by operation of the knob 256 to position the valve member 257 to direct gas either through the tube 258 to supply gas to the nebulizer 91 or, alternatively, through a pseudo or equivalent orifice 259 to provide a flow which is equivalent to the flow through the nebulizer connected to the tub 258 to a tube 261 to a manifold 262 and into an entrainment reservoir 263. This feature allows the ventilator to be employed in a standard pressure cycle mode with conventional nebulization. Additionally, a humidifier mode may be selected to prevent nebulization source gas from being delivered into the breathing circuit during volume cycled procedures when a humidifier is employed.

The sequencing servo 121 can be switched from "off" to "on" either on a patient spontaneous assist or time delay controlled basis. When a physiological inspiratory pressure drop is created in the patient breathing circuit 86, this pressure drop is transmitted through the reverse flow check valve 264 into the manifold created by the bellows 37 through the sensing/servoing venturi 192 into the entrainment port 266 through a tube 267 to a manifold 268 which is in communication with the chamber 124 provided on one side of the diaphragm 123 to act upon the diaphragm to cause a servoing force to move the valve member 122 to an open position. Thus, it can be seen that a physiological inspiratory pressure drop will cause the sequencing servo 121 to servo "on" and to cause a spontaneous inspiratory effort by the patient to be assisted by a positive inspiratory flow of gas under pressure from the ventilator.

When a controlled inspiratory frequency is programmed in the ventilator, the expiratory timing cartridge 138 is utilized to servo the sequencing servo 121 into an "on" or inspiratory phase. The normally open expiratory timer cartridge 138 receives source gas from the master on-off switch 106 through the tube 136. Gas flows through the normally open expiratory timer cartridge 138 through a tube 270 to a tee 269. One leg of the tee 269 is connected by tube 271 to a jet 272 of the sensing/servoing venturi assembly 192. When the venturi 273 in the venturi assembly 192 is activated by essentially a 50 psi drop across the orifice, the pressure in the entrainment port 266 becomes sub-ambient. This sub-ambient condition is supplied through the tube 267 to the manifold 268 and to the chamber 124 to cause the diaphragm 123 to move the valve member 122 to an open position to servo the sequencing servo 121 to the "on" or inspiratory condition. By way of example, a sub-ambient pressure of over 5 cm of water can be generated with distal venturi pressures of over 50 cm of water allowing the sequencing servo to sequence "on" against post end expiratory pressures in excess of 50 cm of water. The starting effort to sequence the sequencing servo 121 into an "on" position can be programmed by adjustment of the compound knob assembly 126.

The timing circuit of the expiratory timing cartridge 138 consists of the one-way check valve 179 delivering gas into a reservoir 181 which serves as a time accumulator and which is in communication with the chamber 142. An expiratory time control metering valve 273 adjusts operation of the knob which controls the bleed-down of gas under pressure in the chamber 142 through a tube 276 through the post-inspiratory hold/expiratory time interlock check valve 277 and line 278 into the manifold 207 and line 208 into the manifold 209.

The expiratory timing circuit is preferentially charged by the sequencing servo 121 whenever and as long as the sequencing servo remains in the on inspiratory phase. When the sequencing servo 121 servoes off and the exhalation valve section of the common inspiratory circuit including the tube 212 is depressurized as hereinafter described, bleed-down of the expiratory timer circuit commences at a rate determined by the adjustment of the needle valve 273. When the servoing diaphragm 141 of the expiratory timing cartridge 138 is sufficiently depressurized, the poppet gate valve 139 opens gradually servoing the sensing/servoing venturi jet causing the sequencing servo 121 to be servoed on into the inspiratory phase.

The sequencing servo 121 is servoed or cycled from on to off by a pressure rise acting upon the servoing diaphragm 123. This pressure rise is sensed through the entrainment port 266 of the tube 267 and is supplied to the chamber 124. When the pressure acting upon the diaphragm 123 is sufficient to overcome the holding force of the magnetic clutch utilized therein, the valve member 122 is moved to the closed position and the sequencing servo is sequenced to the off position.

The sequencing servo 121 can also be servoed to the off position and into the inspiratory phase with volume cycling. The bellows 37 as it moves up and down carrying with it the push rod 46 engages the operating member 79 of the volume termination switch to move the valve member 281 from an open to a closed position against the force of a spring 282. Overcenter travel of the volume termination switch 78 allows the top end of the volume cycling push rod 46 to serve as a mechanical stop. When the upward movement of the push rod 46 is arrested and the bottom wall of the bellows is prevented from traveling upward. Servoing pressures around the bellows and within the canister 38 then rise until the pressure is transmitted through the large tube 283 to the sensing/servoing venturi assembly 192 to the entrainment port 266 through the tube 267 and to the chamber 124 on one side of the diaphragm 123 to cause it to move upwardly to move the valve member 122 to a closed position to sequence the sequencing servo 121 to the "off" position and to commence the expiratory phase.

Alternatively, when the volume termination switch 78 is operated, the sequencing servo 121 will also be switched to the "off" position. This occurs because source gas during the inspiratory phase is being supplied through the normally open volume sequencing delay cartridge 229 through the tube 231 to the volume termination switch 78. As soon as the valve member 281 is moved to the open position, this gas flows through a tube 286 to a tee 287. The tee 287 is connected to another tee 288 which is connected to a pneumatic wink light 289. The tee 288 is also connected to a one-way check valve 290 which is connected by tube 291 to the manifold 268 which is in communication with the chamber 124. Thus, it can be seen that as soon as the termination switch 78 is moved to the open position, gas will be supplied under pressure to the chamber 124 to cause the diaphragm 123 to move the valve member 122 to the closed position. Gas is also supplied from the tee 287 through a loading orifice 292 through a one-way check valve 293 to pressurize a chamber 294 provided on one side of a diaphragm 296 to cause it to move the valve member 204 against the force of the spring 206 to a closed position for the post-inspiratory hold time control cartridge 203. The bleed-down from the chamber 294 is through an orifice 301 open to the atmosphere at a controlled rate as determined by a needle valve 302 adjustable in position by use of a knob 303. At the same time, gas is vented from the manifold 268 through the tube 267 to the sensing/servoing venturi to prevent an undue pressure rise within the chamber 124 of the sequencing servo 121.

With the present arrangement of the bellows 37, it can be seen that the volume is measured from the full up position with a residual volume of approximately 500 cc's. The downward travel of the bellows is controlled by the mechanism hereinbefore described. The desired volume is selected by the use of the horizontal dial 71. Since the volume limiting dial 71 protrudes through the front panel, the volume can be easily changed by using the dial as a thumb wheel. The selected tidal volume cannot be rapidly changed and thus serves to protect the physiological structures against a mass of inadvertent volume shift. As can be seen from the foregoing description, the ventilator can function as a volume limiting device or a volume servoed ventilator. The volume servoing circuit will cause volume limiting based upon occurrence of a pressure rise.

As hereinbefore explained, the acceleration cartridge 144 receives source gas directly from the master on-off switch 106. The flow acceleration cartridge is a normally closed tapered pneumatic switch. The tapered function is provided by the tapered valve member 146. As also hereinbefore explained, the timing circuit is charged by metered inspiratory flow from the master cartridge 112 through the adjustable needle valve 238. When the poppet valve member 146 is moved to the open position, source gas flows through the outlet through a tube 306. A two-way manifold 307 is mounted on the base line/CPAP cartridge 158. The manifold 307 is connected by a tube 308 to a tee 309. One leg of the tee 309 is connected by a tube 311 to the center jet 312 of the master venturi assembly 219. Peak flow through the flow accelerator cartridge 144 is controlled by the manually adjustable counterspring 147 which applies a yieldable closing force to the tapered poppet valve member 146 and thereby, in effect, controls the opening pressure for the valve member 146. For example, pressures against the diaphragm 148 below approximately 18 psi will not servo the flow accelerator on against the closing piston effect and the counterspring 147. The timing circuit for the flow accelerator cartridge 144 consists of the slope control metering valve 238 and a one-way check valve 313 which serves as a reset device. As shown, the reset check valve 313 is in communication with the chamber 149 and is connected by a tube 314 to the manifold 236. The slope control valve 238 serves to determine the rate at which the timing circuit charges at any given filling pressure and therefore serves to determine the rate of flow acceleration for the ventilator. The inspiratory flow rate valve 238 is normally calibrated to exceed closing pressure (approximately 18 psi) of the flow accelerator cartridge 144 when opened (counterclockwise) at approximately the eleven o'clock position. As the inspiratory flow rate valve 238 is progressively opened, the rate of onset of flow acceleration is increased until in the full open position of the valve 238, the onset of flow acceleration is almost instantaneous.

During the expiratory phase, the flow accelerator timing circuit is dumped through the reset valve 313 into the depressurized inspiratory flow circuit. The reset valve 313 only remains competent when the inspiratory flow circuit is charged.

As hereinbefore explained, post inspiratory hold apneustic flow and time are provided in the ventilator. Variable time is provided by the post inspiratory hold time control cartridge 203 which is installed in the exhalation valve segment of the inspiratory circuit of the ventilator. The inlet of this cartridge 203 provides gas to serve the exhalation valve through the manifold 207, the tubes 208 and 212 to the exhalation valve. It also provides flow from the tube 208 through the manifold 209 to the inlet of the master cartridge/inspiratory flow failsafe lockout cartridge 211. It also supplies gas from the manifold 207 through the tube 278 to the one-way valve 277 which serves as a post inspiratory hold/expiratory time interlock device. Thus, it can be seen that the outlet of the post inspiratory hold cartridge 203 is connected directly into the mechanical inspiratory flow circuit.

Charging of the post inspiratory hold timing circuit occurs when the volume termination switch 78 is servoed to the open position. Gas is supplied from the volume termination switch 78 through the tube 286, tee 287, loading orifice 292, the one-way check valve 293 and then into the chamber 294 to pressurize the servoing diaphragm 296 in the post inspiratory hold time control cartridge 203. This causes the post inspiratory hold/expiratory time interlock device to be held competent and the exhalation valve connected to the tube 212 to remain closed. This ensures that a pre-selected mechanical tidal volume must be delivered before a post inspiratory hold can occur.

The post inspiratory time for the apneustic hold is controlled by bleeding down the timing circuit for the cartridge 203 through the adjustable metering valve 302 which can be programmed by adjustment of the knob 303 to allow the selection of static post inspiratory hold periods ranging from 0.25 to 3 seconds by preventing the exhalation valve connected to the tube 212 from opening. In addition, the post inspiratory hold/expiratory timer interlock device 277 is held competent by preventing bleed-down of the expiratory timing circuit during the apneustic hold and thereby allowing the programmed expiratory time to start timing out at the end of the post inspiratory hold period instead of at the end of expiration. Without the interlock device 277, the ventilator could deprogram to mechanically enter into an inspiratory phase during a post inspiratory hold.

Apneustic flow which can be identified as dynamic post inspiratory flow during hold is provided by a normally open expiratory flow cartridge 152 which also can be identified as an expiratory nebulization cartridge when the expiratory flow is provided through the jet of a nebulizer for humidification during augmented spontaneous ventilation. Source gas is supplied to the cartridge from the master on/off switch 106 through the tube 136, the manifold 137 through tube 151 to the inlet of the expiratory flow cartridge 152 to the outlet through a tube 316, through an expiratory nebulization control valve assembly 317 which is provided with a needle valve 318 that can be adjustably positioned by a control knob 319. The adjusted flow through the valve assembly 317 is supplied to a tube 321 which is connected to the nebulizer 91 for humidification during augmented spontaneous ventilation.

During the mechanical inspiratory phase, the expiratory flow cartridge 152 is servoed into the closed position by flow/pressure of gas from the sequencing servo 121. Gas is supplied from the outlet manifold 167 of the sequencing servo 121 through the tube 176, tee 177, tube 182, through the expiratory timer preferential loading orifice 183, tube 184, tee 186, tube 193 to the twin manifold 194 to pressurize the chamber 156 to cause the diaphragm 154 to move the valve member 153 to the closed position. During the mechanical expiratory phase of the sequencing servo 121, the expiratory flow cartridge 152 is in the open position.

As hereinbefore explained, the expiratory flow is metered through the valve assembly 317 by an adjustable metering valve to provide a constant expiratory flow of up to 200 cc a second. If desired, rather than directing the expiratory flow through the nebulizer 91, as hereinbefore described, the expiratory flow can be introduced into an auxiliary inlet port connected into the patient adapter 93.

From the foregoing it can be seen that apneustic time and flow can be independently selected to provide control over the distribution and volume of equalizing pulmonary gases supplied to the patient.

The operation and function of the volume sequencing delay cartridge 229 can now be described. Without such a cartridge 229, the ventilator when programmed to deliver a minimum tidal volume at rapid rates could "step ladder". By this it is meant that the inspiratory time might not be sufficiently long to load the inspiratory timing circuit causing an immediate inspiratory cycling after the volume termination switch 78 servoed the sequencing servo switch 121 off. This would provide an insufficient time for the exhalation valve segment of the inspiratory circuit to bleed-down causing one volume to be delivered upon another because the exhalation valve would not open during the very limited expiratory phase. This could result in a lockout or a high inspiratory pressure venting through the overpressure governor (not shown). Such step-ladder ventilation is prevented by employing the volume sequencing by employing the volume sequencing delay cartridge 229. This delay cartridge 229 is provided with a valve member 326 which is held in a normally open position by spring 327. The valve member is moved to a closed position by diaphragm 328 when gas under pressure is supplied to a chamber 329. As hereinbefore explained, with the volume sequencing delay cartridge 229 in the normally open position, source gas is supplied to the tube 231 to the inlet of the volume termination switch 278.

The timing circuit of the volume sequencing delay cartridge flow is loaded by servoing of a flow/pressure from the expiratory timing cartridge 138. As soon as the valve member 139 of the cartridge 138 moves to its normally open position, source gas is supplied through the tube 270 through the tee 269 through a one-way check valve 331, tube 332, tee 333, tube 334 into the chamber 329. A bleed-down orifice 336 is connected to the other leg of the tee 333. Thus, it can be seen that when the expiratory timing cartridge 138 is permitted to return to its normally open position, the timing circuit for the volume sequencing delay cartridge 229 is pressurized which causes its diaphragm 328 to move the valve member 326 to a closed position preventing inspiratory gas from servoing the sequencing switch by operation of the volume termination switch 78.

The fixed bleed-down orifice 336 open to the atmosphere will bleed-down the gas in the chamber 329 so that the valve member 326 will open in a predetermined time as, for example, in approximately one second. Therefore, the inspiratory time in the volume limiting mode of the ventilator cannot be programmed under one second or any other predetermined time as determined by the size of the fixed orifice 336 preventing "step ladder" ventilation.

During the one second inspiratory time caused by the delay of gases flowing to the volume termination switch 78, the expiratory timing circuit has sufficient time to be charged maintaining a minimal expiratory time of one second when the ventilator is programmed for a minimal expiratory time.

The failsafe lockout system which is provided in the ventilator is comprised of the normally open master cartridge/inspiratory flow failsafe lockout cartridge 211 which, when open, vents the exhalation valve segment which includes the tube 212 of the inspiratory circuit to ambient through the tube 248 and the alarm 249. Servoing or opening of the failsafe lockout cartridge 211 is provided by a timing circuit hereinbefore described. During the mechanical inspiratory phase, flow/pressure is delivered through the master flow cartridge 112 to the inlet manifold 227 where gas is delivered at an adjustable controlled rate by valve member 242 into the chamber 243 and into the outlet side of the reset valve 251. During the expiratory phase, high pressure gases in the failsafe timing circuit are vented from the chamber 243 through the reset valve 251 into the depressurized inspiratory circuit.

Charging of the failsafe timing circuit for the failsafe lockout cartridge 211 commences at the beginning of the mechanical inspiratory phase. The rate of charging to the actual time of servo or opening of the normally closed valve 246 is dependent upon the pressure of the gases in the inspiratory circuit and the adjustment of the valve member 242 to control the metering of gases into the chamber 243. Normally, the valve member 242 would be adjusted against mean inspiratory circuit pressures to lockout at between five to six seconds. When the valve member 246 is moved to the open position venting the tube 212 to the atmosphere, the exhalation valve assembly 94 is rendered incompetent, venting mechanical inspiratory and physiological expiratory flows to ambient.

Whenever the jets 218 and 312 of the master venturi assembly 219 are pressurized sufficiently to produce a gas entrainment gradient, flow is induced through an entrainment port 338 provided in the manifold 262 from the entrainment reservoir 263. The entrainment port 338 is normally closed by a gate valve 339 which is held in this position by a spring 341. The reservoir 263 is of the distensible type and contains gas of the desired oxygen concentration for the patient. Without such a reservoir, ambient air would be entrained by the ventilator which would upset the final oxygen concentration in the gas for the patient.

Since the demands on the entrainment reservoir are variable, it is desirable to employ an automatic entrainment reservoir refill system which comprises the entrainment reservoir refill servo cartridge 128 which is provided with a chamber 342 that is in communication with the manifold 262 connected to the entrainment reservoir 263 so that the diaphragm 131 can sense the pressure of gases in the reservoir 263. The piston effect of the 50 psi inlet gas against the valve member 129 tends to open the valve member and an adjustable counterspring 132 provides a closing force. Normally the counterspring 132 is adjusted to require a positive pressure against a servoing diaphragm of approximately 8 centimeters of water ($H_2O$) to effect a sufficient closing force to contain a flow from the cartridge 128. Consequently, whenever the pressures within the entrainment reservoir 263 fall below approximately 8 centimeters of water, the closing force against the diaphragm 131 is overcome and the valve member 129 moves to the open position as is supplied through a tube 344 to the manifold 263 and into the entrainment reservoir 263. Filling of the reservoir 263 continues until the pressure of the gas in the reservoir as measured by the diaphragm 131 overcomes the piston effect of the source gases and moves the valve member 129 to a closed position. It should be appreciated that when the humidifier mode is selected by the use of the inspiratory nebulizer/humidifier selector switch 197, source gas can be delivered from the manifold 196 through the orifice 259, the tube 261 into the manifold 262 and into the entrainment reservoir 263. This flow of gas into the entrainment reservoir 263 when this mode is selected serves as a means of balancing the systemic inspiratory pressures regardless of which mode is selected by the selector switch 197.

The pressurization limits of the entrainment reservoir 263 are controlled by the side of the accessory entrainment gate valve 339 which is set to open at approximately 10 centimeters of water and, in addition, by an emergency entrainment gate valve assembly 346 which includes a gate valve 347 held in a closed position by a spring 348 and an alarm 349 in the form of an orifice whistle which gives an audible indication when emergency air is being introduced through the emergency entrainment valve assembly 346.

Under normal ventilatory conditions with the demand CPAP being operative, the operator may adjust the sensitivity of the entrainment reservoir refill servo or cartridge 128 to just provide for refill with a further refill flow reduction causing ambient air entrainment. As ambient air is entrained through the emergency intake alarm 349 an audible whistle may be heard. The operator may then gradually increase refill flow until the alarm is muted by sufficient refilling flow from the entrainment servo 128. With proper refill established for the entrainment reservoir 263, a disconnect in the patient breathing circuit should stop the entire inspiratory delivery pressure sufficiently to cause a venturi entrainment in excess of the adjusted limit of the entrainment reservoir refill servo 128. When the entrainment reservoir 263 is evacuated by the venturi demand, ambient air will be entrained through the emergency alarm to sound an alarm. Thus, an alarm will be actuated upon a disconnect in the patient breathing circuit.

The demand CPAP system which is utilized within the ventilator comprises the baseline CPAP cartridge 158. The inlet is supplied with gas through the tube 157 through the tube 136 from the master on-off switch 106. The outlet manifold 307 delivers gas through a tube 308, tee 309, tube 311 to the center jet 312 of the master venturi assembly 219. The diaphragm 161 which is provided with a chamber 166 on one side thereof of the cartridge 158 is in communication with the interior of the bellows 37 by a tube 351. Opening forces for the cartridge 158 are provided by the source gases upon the valve member 159 and the balance spring 162. Closing forces are delivered by an adjustable spring 163 as well as the positive pressure in the chamber 166 acting upon the diaphragm 161. The positive pressure is maintained in the breathing circuit when the spring 163 is adjusted to a relaxed condition to permit a certain degree of flow upon demand until a specific positive counterpressure acts upon the diaphragm 161 to close the poppet valve 159. The more the counterspring 163 is relaxed, the greater the positive counterpressure against the diaphragm from pressure within the chamber 166 to cause closing of the poppet valve 159. Therefore, specific positive pressures (baselines) can be precisely selected within the breathing circuit for maintenance during physiological end expiration.

The adjustable demand CPAP sensitivity orifice 201 plays a major role in the augmentation of spontaneous respiration while maintaining a positive end expiratory pressure. This orifice includes an adjustable valve member 352 which controls the flow of source gas through the tube 213 and through the tube 217 to the auxiliary orifices 218 of the master venturi assembly 219. Source gas is supplied past the adjustable valve member 352 through a one-way check valve 353 which is connected by a tube 354 to the tee 309. Thus, it can be seen that the demand CPAP sensitivity orifice 201 determines the flow/pressure entering the outflow control segment of the breathing circuit. In the exhalation valve assembly 94, the exhalation valve serves as the outflow valve and is servoed by very accurately controlling the pressures acting against the servoing diaphragm. The flow/pressure against the exhalation valve diaphragm is balanced against the dual jets 312 and 218 of the master venturi assembly 219 and the inspiratory nebulizers/humidifier orifices. For any given servoing pressure against the inlet of the CPAP sensitivity orifice 201, the downstream pressures within the outflow valve control circuit can be controlled. As the orifice is opened, the pressures within the entire demand CPAP circuit come into equilibrium causing stiff clutching of the outflow valve with a sluggish physiological response. As the CPAP sensitivity orifice is metered down, pressures in the outflow of the valve control circuit are decreased causing a greater clutching of the outflow providing a more rapid response to breathing circuit pressure change during augmented spontaneous respiration. Therefore, response time and thus work of breathing may be mechanically controlled.

For any given baseline established, the demand flow accelerator or CPAP cartridge 158 will respond to pressure changes within the mechanical/physiological breathing circuit. As pressures drop away from baseline, inflow is accelerated to meet physiological inspiratory demands. As circuit pressures rise, inflow is retarded until total flow shutdown occurs as pressure rises through approximately 3 centimeters of $H_2O$ above baseline (this would occur during mechanical inspiratory volume delivery). The cartridge 158 is programmed to allow a drop away from the baseline between 2 and 3 centimeters of $H_2O$ during augmented spontaneous inspiration.

It can be seen that the cartridge 158 serves as a post end expiratory pressure generator automatically remaining off (out of the circuit) during mechanical inspiration/expiration until reaching the baseline and thereby eliminating a major source of mechanical retard during peak physiological expiratory flow.

During demand CPAP procedures when spontaneous respiration is being augmented while maintaining a positive end expiratory pressure, the bellows circuit is passive. Inspiratory gas flow generated in the master venturi 219 flows through the bellows manifold 356 and out through the transfer valve assembly 357. The transfer valve assembly 357 includes a valve member 358 which is actuated by a diaphragm 359. A chamber 361 is provided on one side of the diaphragm 359. Gas, after it passes through the transfer valve assembly 357, passes through the reverse flow check valve 264 and through the outlet 86 into the breathing circuit to satisfy the physiological inspiratory demands of the patient. Pressures within the entire bellows circuit in the manifold 356, in the container 38 outside the bellows, and within the bellows 37 equalize producing a flow gradient to the proximal physiological airway 86.

During either pressure or volume cycled (assisted or controlled) tidal volume delivery, the transfer valve 358 is moved to a closed position by source gas pressure being supplied from the sequencing servo 121 through the line 168, the manifold 169, the tube 171, and through the one-way valve 174 into the chamber 361. As soon as the transfer valve 358 is closed, the interior of the bellows 377 is isolated from the exterior of the bellows within the container 38. When this is the case, the inspiratory flow of gas generated by the master venturi 219 is directed downwardly through a large tube 283 into the container 338 and exterior of the bellows 37. As the pressure of the gases in the container 38 and exterior of the bellows 37 begins to rise, the bellows 37 are servoed upwardly displacing the internal volume of gases within the bellows 37 through the reverse flow check valve 264 and into the breathing outlet 86 and into the breathing circuit.

When the inspiratory cycling pressure volume is reached, the sequencing servo 121 is switched into the expiratory phase as hereinbefore described. When this occurs, gas under pressure is no longer supplied to the chamber 361 and the gas in chamber 361 is bled off through the bleed-down orifice 173 and into the depressurized inspiratory circuit. The transfer valve 358 then moves to an open position. After internal and external bellows pressures are equalized by the volume stabilizer valve assembly 169 as hereinafter described, the bellows 37 under the force of gravity will descend into the canister 38 displacing gas external of the bellows into the tube 283 through the manifold 352 and into the interior of the bellows 37. By transferring the gases which were utilized for causing upward movement of the bellows 37 into the interior of the bellows for later use by the patient, the cost of operation of gases for the ventilator is reduced. Bellows entrainment gases from the breathing circuit is negated by the reverse flow check valve 264. Thus, it can be seen that the flow-through breathing circuit hereinbefore described makes it possible to provide intermittent mandatory ventilation or any form of mechanical ventilation employing a combination of spontaneous and controlled respiration. If the volume transfer valve 358 should open before the exhalation valve 94, the pressure in the cannister 38 surrounding the bellows 37 could be released into the breathing circuit 86 to cause a brief pressure rise. Such a brief pressure rise is prevented by the volume stabilizer valve assembly 169 which is connected to the master venturi 219 between the venturi entrainment port and the accessory entrainment gate valve 339 and has an outlet 369 open to the atmosphere. The volume stabilizer valve assembly 169 includes a valve member 366 operated by a diaphragm 367 normally held in a closed position by a spring 368 and has a chamber 371 on one side of the diaphragm 367. The volume stabilizer valve assembly 169 is normally closed but not competent so that it allows one-way flow of gas in the master venturi 219 to the atmosphere. During mechanical inspiration, however, the gas volume stabilizer valve member 366 is held competent by gas that flows from the sequencing servo 121 through the tube 168 to the chamber 371. That gas also flows through a one-way check valve 174 and a fixed orifice 173 to the transfer valve assembly 357 so that both the transfer and volume stabilizer valve assemblies 357 and 169 are simultaneously closed. At the start of mechanical expiration, gas pressure in the volume stabilizer valve assembly 357 is released before the gas pressure is released in the volume transfer valve assembly 169 due to the orifice 173 (as is the gas pressure in the exhalation valve 94) so that gas above ambient pressure in the cannister 38 exterior of the bellows 37 will be vented to the atmosphere through the outlet 369 before the volume transfer valve assembly 199 is opened.

A panel-mounted manometer 376 is connected by a tube 377 through an orifice 378 to the proximal airway at the patient adapter 93.

An emergency inlet assembly 381 is provided in the outlet tube 86 and includes a gate valve member 382 normally held in a closed position by a spring 383. The breathing tube assembly 92 includes a conventional water trap assembly 384.

What is claimed is:

1. In a volume limiting ventilator having an inhalation phase and an exhalation phase in its operative cycle for use with a source of gas under pressure, an inlet adapted to be connected to the source of gas, a rigid canister, an expandable and collapsible bellows in said canister forming a chamber inside the bellows and in cooperation with the canister forming a chamber exterior of the bellows, a patient adapter adapted to be connected to the airway of the patient, means for connecting the patient adapter to the chamber within the bellows, flow path means for connecting the chamber exterior of the bellows and the chamber inside the bellows, transfer valve means mounted in said flow path means for controlling the flow of gases through the flow path means, a sequencing servo having an inlet connected to the inlet of the ventilator, an outlet, and a valve member movable between open and closed positions for controlling the flow of gases from the inlet to the outlet of the sequencing servo to cause the inhalation phase and the exhalation phase respectively of the ventilator, diaphragm-operated means for moving the valve member between its open and closed positions, means coupled to the sequencing servo for adjusting the forces applied to the diaphragm, a master venturi assembly and a sensing venturi assembly coupled to the flow path means both between the chamber exterior of the bellows and the transfer valve means, means for connecting the sensing servo assembly to the diaphragm-operated means of the sequencing servo so that pressure sensed by the sensing venturi assembly is supplied to the sequencing servo assembly, means connected between the outlet of the sequencing servo assembly and the master venturi assembly for supplying source gas to the master venturi during the inhalation phase, means connected between the inlet of the ventilator and the sensing venturi assembly for supplying source gas to the sensing venturi at the commencement of the exhalation phase, an exhalation valve assembly having an inlet connected to the patient adapter and an outlet vented to the atmosphere, means for supplying source gas from the sequencing servo during the inhalation phase to maintain the exhalation valve assembly in a closed position, a volume stabilizer valve assembly coupled to the master venturi assembly, said transfer valve assembly and said volume stabilizer valve assembly each having a valve member movable between open and closed positions and diaphragm-operated means for moving their valve member toward one of said positions, and means for supplying source gas to said diaphragm-operated means of said transfer valve assembly and said volume stabilizer valve assembly to simultaneously move their valve members to closed positions during the inhalation phase including means for causing a delayed opening of the valve member for the transfer valve assembly at the commencement of the exhalation phase, thereby causing opening of the volume stabilizer valve assembly prior to opening of the volume transfer and exhalation valve assemblies at the end of inhalation so that the gas volume above ambient pressure in the chamber exterior of the bellows will be vented to ambient.

2. A ventilator as in claim 1 together with means carried by the bellows for limiting the travel of said bellows downwardly into the canister to thereby limit the maximum volume of the chamber formed by the bellows.

3. A ventilator as in claim 2 together with a jack screw, a volume limiting dial accessible to the operator for rotating the jack screw and means carried by the jack screw and adapted to be engaged by the means for limiting the downward travel of the bellows in the canister.

4. A ventilator as in claim 3 together with visual means for indicating the position of the bellows and thereby giving an indication of the volume of gas within the chamber in the bellows.

5. A ventilator as in claim 1 wherein said means for causing a delayed opening for the transfer valve assembly includes a one-way valve and a restricted orifice connected in parallel to the diaphragm operated means of the transfer valve assembly.

6. A ventilator as in claim 1 together with expiratory time control means having an inlet connected to the source of gas under pressure and an outlet and valve means movable between open and closed positions for connecting the flow of gas from the inlet to the outlet of the expiratory time control means, means connecting the outlet of the expiratory time control means to the sensing venturi assembly, volume sequencing delay means having an inlet and an outlet and a valve member movable between open and closed positions for controlling the flow of gas from the inlet to the outlet, diaphragm operated means for moving the valve member between open and closed positions and means for supplying gas from the outlet of the expiratory timing means to the diaphragm operated means, bleed-down means connected to the diaphragm operated means of the sequencing delay cartridge for bleeding down the sequencing delay cartridge within a predetermined period of time, diaphragm operated means for moving the valve member of the expiratory time control means between open and closed positions, means for supplying gas from the outlet of the sequencing servo to the diaphragm operated means of the expiratory time control means, a volume termination switch adapted to be controlled by movement of the bellows in the canister, means for supplying gas under pressure through the volume sequencing and delay means to the volume termination switch so that gas cannot be supplied to the volume termination switch until a predetermined time has elapsed as determined by the volume sequencing delay means to permit the expiratory timing means to operate and to prevent a build-up of gas under pressure in the expiratory time control means.

7. A ventilator as in claim 1 together with failsafe lock-out means having an inlet and an outlet and a valve member movable between open and closed positions to control the flow of gas from the inlet to the outlet and diaphragm operated means for controlling the movement of the valve member, means connecting the outlet of the failsafe lock-out means to the exhalation valve assembly, timing means coupled to the diaphragm operated means of the fail-safe lockout means and to the outlet of the sequencing servo so that source gas is supplied to the timing means during the inhalation phase so that the valve member of the failsafe lockout means is moved to the open position after a predetermined time to vent the exhalation valve assmbly to the atmosphere.

8. A ventilator as in claim 7 wherein said timing means includes an adjustable metering valve for metering source gas to the diaphragm operated means and one-way reset valve means connected in parallel with the adjustable metering valve for resetting of the failsafe lock-out means at the commencement of the exhalation phase.

9. A ventilator as in claim 1 together with a master flow means having an inlet and an outlet valve member movable between open and closed positions for controlling the flow of gas from the inlet to the outlet and diaphragm operated means for controlling the movement of the valve member, means connecting the inlet of the master flow means to the inlet of the ventilator, means connecting the outlet of the master flow means to the master venturi and means connecting the diaphragm operated means of the master flow means to the outlet of the sequencing servo.

10. A ventilator as in claim 1 together with an entrainment reservoir coupled to the master venturi assembly, a one-way gate valve for preventing the flow of gas from the master venturi assembly into the entrainment reservoir and for permitting a flow of gas from the entrainment reservoir into the master venturi assembly, entrainment reservoir refill means having an inlet and an outlet and a valve member moveable between open and closed position for controlling the flow of gas from the inlet to the outlet and an adjustable diaphragm operated means for controlling the movement of the valve member, means connecting the inlet of the entrainment reservoir refill servo means to the inlet of the ventilator, means connecting the outlet of the entrainment reservoir refill means to the entrainment reservoir and means coupling the entrainment reservoir to the diaphragm operated means of the entrainment reservoir refill means so that when a reduction in pressure of gas in the entrainment reservoir occurs, the diaphragm operated means of the entrainment reservoir refill means will move the valve member to an open position to permit gas to flow to refill the entrainment reservoir.

11. A ventilator as in claim 1 together with a port for supplying gases for inspiratory nebulization, inspiratory nebulizer selector means having an inlet and first and second outlets, means connecting the inlet of the inspiratory nebulizer selector means to the outlet of the sequencing servo, means connecting the first outlet of the inspiratory nebulizer means to the inspiratory nebulization port, means connecting the second outlet of the inspiratory nebulizer selector means to the entrainment reservoir, said inspiratory nebulizer selector means including a valve member movable between two positions for permitting gas from the inlet to flow either to the first outlet to the inspiratory nebulization port or alternatively to the second outlet and to the entrainment reservoir.

12. A ventilator as in claim 11 together with a restricted orifice connected to the second outlet of the inspiratory nebulizer selector means so that the flow of gas to the entrainment reservoir is at the same rate as the flow to the inspiratory nebulization port.

13. In a volume limiting ventilator having an inhalation phase and an exhalation phase in its operative cycle for use with a source of gas under pressure, an inlet adapted to be connected to the source of gas, a sequencing servo having an inlet connected to the inlet of the ventilator, an outlet, a valve member movable between open and closed positions for controlling the flow of gases from the inlet to the outlet, and diaphragm-operated means for moving the valve member between open and closed positions, a patient adapter, a master venturi assembly connected to the patient adapter, means connected between the outlet of the sequencing servo and the master venturi for supplying source gases to the master venturi, an exhalation valve assembly having an inlet connected to the patient adapter and an outlet vented to the atmosphere, means for supplying source gas from the sequencing servo to the exhalation valve assembly during the inhalation phase to maintain the exhalation valve assembly in a closed position, an inspiratory nebulization port, nebulizer means adapted to be connected between the nebulization port and the patient adapter, inspiratory nebulizer selector means having an inlet and first and second outlets and valve means for selecting passage of gases from the inlet to either the first outlet or the second outlet, means connecting the first outlet to the inspiratory nebulization port, an entrainment reservoir coupled to the master venturi assembly, means coupling the second outlet to the entrainment reservoir, and means coupling the inlet of the inspiratory nebulizer selector means to the outlet of the sequencing servo whereby a continuous flow of gas is supplied either to the inspiratory nebulization port or alternatively to the entrainment reservoir during the inhalation phase.

14. A ventilator as in claim 13 together with restricted orifice means for restricting the flow to the entrainment reservoir so that it is the same rate as supplied to the inspiratory nebulization port when it is selected.

15. A ventilator as in claim 13 together with failsafe lock-out means coupled to the exhalation valve assembly, said failsafe lock-out means including an inlet and an outlet and a valve member movable between open and closed position for controlling the flow of gas from the inlet to the outlet and diaphragm operated means for operating the valve member, means coupling the outlet of the failsafe lock-out means to the outlet of the sequencing servo and to the exhalation valve assembly so that gas is supplied thereto during the inhalation phase, the outlet of the failsafe lock-out means being open to the atmosphere and timing means coupled to the diaphragm operated means of the failsafe lock-out means so that the valve member of the failsafe lock-out means is moved to the open position after a predetermined period of time.

16. A ventilator as in claim 15 wherein said timing means includes means coupling the same to the source gas during inhalation phase and adjustable means for controlling the flow of source gas to the diaphragm operated means and one-way check valve means for permitting resetting of said failsafe lock-out means at the termination of the inhalation phase.

17. A ventilator as in claim 13 wherein said means coupling the master venturi assembly to the patient adaptor includes a rigid canister, an expandable and collapsable bellows in said canister forming a chamber interior of the bellows and in cooperation with the canister forming a chamber exterior of the bellows, means connecting the patient adapter to the chamber within the bellows, flow path means establish communication between the chamber exterior of the bellows and the chamber interior of the bellows, transfer valve means mounted in said flow passage for controlling the flow of gases through the flow path means, means coupled to the outlet of the sequencing servo and to the transfer valve means for moving the transfer valve means to the closed position during the inhalation phase to prevent the flow of gas from the chamber exterior of the bellows to the chamber interior of the bellows and means carried by the bellows for limiting the travel of the bellows downwardly into the canister.

18. A ventilator as in claim 17 together with volume stabilizer means coupled to the master venturi assembly and open to the atmosphere and having a valve member movable to a position to prevent the master venturi from being vented to the atmosphere and means coupled to the outlet of the sequencing servo for maintaining said valve member of the volume stabilizer in a closed position during the inhalation phase.

19. A ventilator as in claim 17 wherein said means for limiting the downward travel of the bellow in the canister includes a rotatably mounted jack screw, a volume limiting dial accessable to the operator for rotating the jack screw and means carried by the jack screw adapted to be engaged by the means for limiting downward travel of the bellows in the canister.

20. A volume limiting ventilator having an inhalation phase and an exhalation phase in its operative cycle for use with a source of gas under pressure, an inlet adapted to be connected to the source of gas, a rigid canister, expandable and collapsible bellows in said canister forming a chamber inside the bellows and in cooperation with the canister forming a chamber exterior of the bellows, a patient adapter adapted to be connected to the airway of the patient, means for connecting the patient adapter to the chamber within the bellows, flow path means for connecting the chamber exterior of the bellows and the chamber inside the bellows, transfer valve means mounted in said flow path means for controlling the flow of gas through the flow path means, a sequencing serve having an inlet connected to the inlet of the ventilator, an outlet, and a valve member movable between open and closed positions for controlling the flow of gas from the inlet to the outlet, and diaphragm-operated means for moving the valve member between its open and closed positions, a master venturi assembly coupled to said flow path means between the chamber exterior of the bellows and the transfer valve means, means connected between the outlet of the sequencing servo and the master venturi for supplying source gases to the master venturi, means fixed to the container for limiting the travel of the bellows in the container, and means adapted to be operated by the means for limiting the movement of the bellows in the container for controlling the operation of the sequencing servo, said means for limiting the travel of the bellows in the canister including a deck plate forming a portion of said canister and to which deck plate one end of said bellows is fixed, a jack screw rotatably mounted in the deck plate, a volume limiting dial rotatably mounted on the deck plate and adapted to be engaged so that it can be rotated by hand, means for coupling the volume limiting dial to the jack screw so that rotation of the volume limiting dial rotates the jack screw, a volume limiting arm threadably engaging said jack screw so as to be moved toward and away from the deck plate as the jack screw is rotated, and a push rod fixed to the bellows, the push rod and the volume limiting arm having portions adapted for engagement to limit the movement of the bellows away from the base plate at a relative position determined by the position of the volume limiting arm on the jack screw.

21. A ventilator as in claim 20 together with the volume indicating rod carried by the push rod and window means carried by the front panel through which the volume indicator rod is visible.

* * * * *